(12) United States Patent
Karamzin et al.

(10) Patent No.: US 11,237,178 B2
(45) Date of Patent: *Feb. 1, 2022

(54) DEVICE FOR MONITORING THE SPATIAL AND TEMPORAL DYNAMICS OF THROMBIN

(71) Applicant: OBSCHESTVO S OGRANICHENNOY OTVETSTVENNOSTYU «HEMACORE LABS», Moscow (RU)

(72) Inventors: Sergey Sergeevich Karamzin, Moscow (RU); Fazoil Inoyatovich Ataullakhanov, Moscow (RU); Aleksey Nikolaevich Nabirkin, Kolomna (RU); Nataljya Mikhajlovna Dashkevich, Pushchino (RU)

(73) Assignee: OBSCHESTVO S OGRANICHENNOY OTVETSTVENNOSTYU <<HEMACORE LABS>>, Moscow (RU)

( * ) Notice: Subject to any disclaimer, the term of this patent is extended or adjusted under 35 U.S.C. 154(b) by 190 days.

This patent is subject to a terminal disclaimer.

(21) Appl. No.: 16/464,175

(22) PCT Filed: Nov. 12, 2017

(86) PCT No.: PCT/RU2017/050116
§ 371 (c)(1),
(2) Date: May 24, 2019

(87) PCT Pub. No.: WO2018/101861
PCT Pub. Date: Jun. 7, 2018

(65) Prior Publication Data
US 2020/0292562 A1 Sep. 17, 2020

(30) Foreign Application Priority Data

Nov. 30, 2016 (RU) ................. 2016147005

(51) Int. Cl.
*G01N 33/86* (2006.01)
*G01N 21/47* (2006.01)
(Continued)

(52) U.S. Cl.
CPC ............. *G01N 33/86* (2013.01); *G01N 21/47* (2013.01); *G01N 21/64* (2013.01);
(Continued)

(58) Field of Classification Search
CPC .... G01N 33/86; G01N 21/47; G01N 21/6486; G01N 33/52; G01N 2021/6439;
(Continued)

(56) References Cited

U.S. PATENT DOCUMENTS 7,767,458 B2    8/2010   Binder
9,958,430 B2 *   5/2018   Ataullakhanov ...... G01N 33/49
(Continued)

FOREIGN PATENT DOCUMENTS

RU     2106627 C1    3/1998
RU      123166 U1   12/2012

OTHER PUBLICATIONS

Translation of RU2106627C1 (Aleksandrov, Andrei Fedorovich; Mar. 10, 1998) (Year: 1998).*

(Continued)

*Primary Examiner* — Jill A Warden
*Assistant Examiner* — Henry H Nguyen
(74) *Attorney, Agent, or Firm* — Volpe Koenig

(57) ABSTRACT

A device for monitoring the spatial and temporal dynamics of thrombin that includes a temperature-controlled sealed chamber with a transparent window and a light trap, the chamber being filled with a fluid medium and designed to accommodate a cuvette containing a test sample of blood plasma, and a coagulation activating insert placed into the cuvette, at least one illumination source and at least one first (Continued)

irradiation source and at least one second irradiation source capable of exciting a fluorescence signal of a special marker that forms in the sample during cleavage of a fluorogenic substrate, a camera, a pressure adjustment element capable of maintaining a pressure inside the chamber, the at least one first irradiation source provides irradiation of the sample in a direction perpendicular to the cuvette, and the at least one second irradiation source provides irradiation of the sample at an angle to the cuvette.

7 Claims, 3 Drawing Sheets

(51) Int. Cl.
      *G01N 21/64*       (2006.01)
      *G01N 33/52*       (2006.01)
      *C12Q 1/56*       (2006.01)

(52) U.S. Cl.
      CPC ......... *G01N 21/6486* (2013.01); *G01N 33/52* (2013.01); *C12Q 1/56* (2013.01); *G01N 21/6408* (2013.01); *G01N 21/6456* (2013.01); *G01N 2021/6439* (2013.01); *G01N 2201/062* (2013.01); *G01N 2333/974* (2013.01)

(58) Field of Classification Search
      CPC ........... G01N 21/6456; G01N 21/6408; G01N 2333/974; G01N 2201/062; G01N 21/64; C12Q 1/56

See application file for complete search history.

(56) References Cited

U.S. PATENT DOCUMENTS

| | | | | |
|---|---|---|---|---|
| 2010/0261211 | A1* | 10/2010 | Ataullakhanov | .. G01N 33/4905 435/13 |
| 2014/0227726 | A1* | 8/2014 | Ataullakhanov | ........ C12Q 1/37 435/13 |
| 2015/0204841 | A1* | 7/2015 | Ataullakhanov | .. G01N 21/0332 422/73 |

OTHER PUBLICATIONS

Dashkevich et al., "Thrombin Activity Propagates in Space During Blood Coagulation as an Excitation Wave", Nov. 2012, Biophysical Journal, 103, 10, 2233-2240 (Year: 2012).*

International Search Report issued in corresponding International Patent Application No. PCT/RU2017/050116 dated Jan. 18, 2018, consisting of 3 pp. (English Translation Provided).

Written Opinion issued in corresponding International Patent Application No. PCT/RU2017/050116 dated Jan. 18, 2018, consisting of 4 pp.

* cited by examiner

DEVICE FOR MONITORING THE SPATIAL AND TEMPORAL DYNAMICS OF THROMBIN

This application is a 35 U.S.C. § 371 national phase application of PCT/RU2017/050116, which was filed Nov. 12, 2017, and claims the benefit of Russian Application No. 2016147005, which was filed Nov. 30, 2016, both of which are incorporated herein by reference as if fully set forth.

FIELD OF INVENTION

This technical decision relates to medicine and biology and can be used in particular for diagnostic and research purposes to determine coagulation characteristics of blood and its components, as well as in biotechnology and in fundamental biological research.

BACKGROUND

The closest prior art is a device disclosed in RF patent No 123166, cl. G01N33/86, published on 20 Dec. 2012. The device includes a temperature-controlled sealed chamber with a transparent window and a light trap, filled with fluid, designed to be capable of receiving inside the chamber of a cuvette containing plasma test sample, wherein the following are placed: a special insert activating coagulation with the substance initiating the coagulation process applied on its butt end; at least one means of illumination of the sample designed to provide the possibility of receiving the light scattering signal from the sample; at least one means of irradiation designed to provide the possibility of excitation of the fluorescence signal from a special marker formed during the process of cleavage of the fluorogenic substrate previously added to the sample by one of proteolytic enzymes of the coagulation system; a means of optical photo/video registration of light scattering/irradiation from the sample; a means for adjusting pressure in the temperature-controlled sealed chamber designed to provide the possibility to maintain within the chamber a pressure exceeding the atmospheric one. As a disadvantage of the said device, one can mention artifact distortion of the marker fluorescence signal at the border between the fibrin clot and non-coagulated blood plasma appearing upon irradiation of the sample by radiation from the excitation of the marker in the direction perpendicular to the cuvette wall. The distortions of the marker fluorescence signal at the fibrin clot growth border lead to mistakes in calculation of concentrations of the proteolytic enzyme, in particular, thrombin in this field of research.

Another disadvantage of the said device is that it does not take into account the influence that the plasma sample optical density has on the fluorescence signal. Thus, the same fluorescence marker concentration shall provide different intensity of the fluorescence signal in normal and turbid plasma (e.g., hemolysis or chylous plasma). As a consequence, it is impossible to use the same calibration for different plasma samples, meaning it is impossible to use the once-established dependence between the fluorescence signal and marker concentration to restore the concentration of the proteolytic enzyme.

SUMMARY

The technical result that can be obtained from implementation of the said technical decision is the improvement of accuracy of definition of the spatial and temporal distribution of thrombin concentration during the process of plasma coagulation, which is necessary to diagnose the status of the blood coagulation system.

The task to be solved by the claimed decision is to eliminate artifact distortion of the marker fluorescence signal at the fibrin clot border and to add the possibility to take into account sample optical density while determining the spatial and temporal distribution of thrombin concentration.

This task is solved by creation of a device for monitoring the spatial and temporal distribution of thrombin comprising a temperature-controlled sealed chamber with a transparent window and a light trap, filled with fluid, designed to be capable of receiving inside the chamber of a cuvette containing plasma test sample, wherein the following are placed: an insert activating coagulation with the substance initiating the coagulation process applied on its butt end; at least one means of illumination of the sample designed to provide the possibility of receiving the light scattering signal from the sample; at least one first means of irradiation designed to provide the possibility of excitation of the fluorescence signal from a special marker formed during the process of cleavage of the fluorogenic substrate previously added to the sample by one of proteolytic enzymes of the coagulation system; a means of optical photo/video registration of light scattering/irradiation from the sample; a means of pressure adjustment in the temperature-controlled sealed chamber designed to provide the possibility to maintain within the chamber a pressure exceeding the atmospheric one; at that, the device contains at least one second means of irradiation designed to provide the possibility of excitation of the fluorescence signal from the said marker; at that, at least one first means of irradiation provides irradiation of the sample in the direction perpendicular to the cuvette plane and at least one second means of irradiation provides irradiation of the sample at an angle to the cuvette plane.

As well as by the fact that it additionally contains the means of analysis of the sample optical density, preferably at the fluorescence marker excitation wavelength.

As well as by the fact that the means of pressure adjustment is designed with the possibility to maintain within the chamber the excess pressure that is 0.2-0.5 atm higher as to the atmospheric one.

As well as by the fact that it contains optical elements that direct, focus, and provide spectral correction of illumination/irradiation.

As well as by the fact that it additionally contains a means of control of the means of illumination/irradiation, photo/video registration and pressure adjustment designed with a possibility to synchronize operation of the said means.

Figure 1:
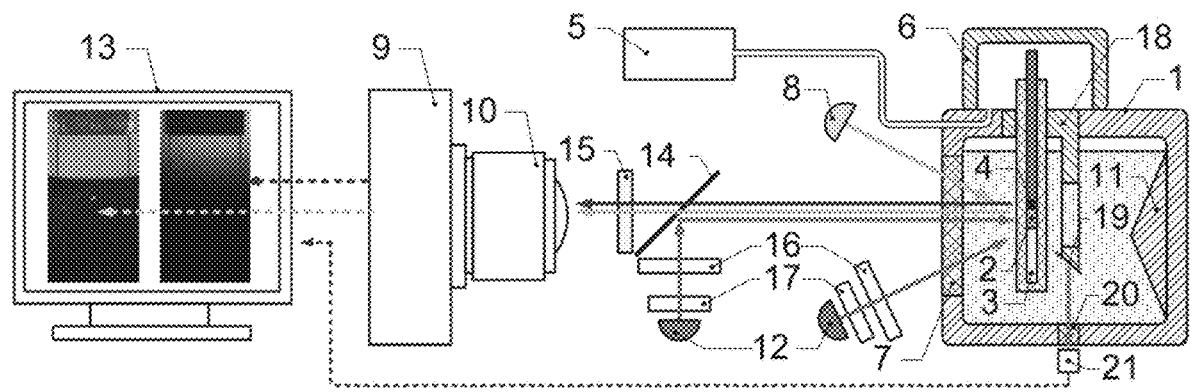
FIG. 1 shows schematic representation of the claimed device.
Figure 2:
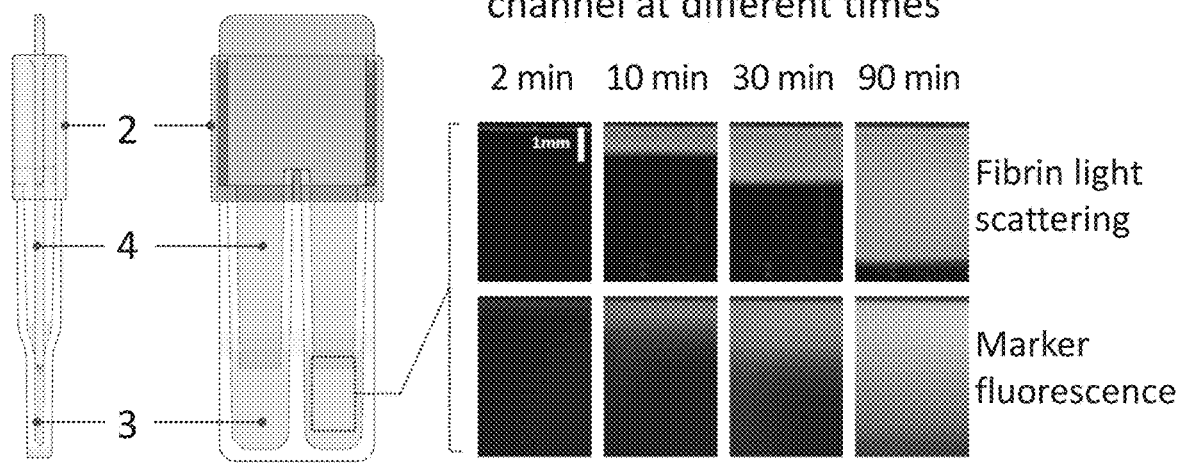
FIG. 2 provides an example of arrangement of the plasma sample and insert-activator in the measuring cuvette, photos of light scattering from the sample illuminated by the means of illumination and photos of the sample fluorescence irradiated by the means of irradiation.

The device (FIG. 1) is intended to determine parameters of the process of coagulation of blood and components thereof and works as follows. Within the sealed, temperature-controlled chamber 1 filled with water or other transparent fluid (hereinafter referred to as «thermal agent»), the temperature of the thermal agent is fixed and maintained at a specific level (per default, 37.0° C.). The cuvette 2 is placed into the temperature-controlled chamber 1 using the cuvette retainer 18. The cuvette 2 can contain one or several chambers. A plasma sample (plasma samples) 3 is (are) placed in the channel (channels) of cuvette 2 (FIG. 2). At that, the cuvette 2 is placed so as to completely immerse the part of the cuvette containing the test sample 3 into the thermal agent, allowing fast and uniform heating of the sample. After the sample 3 is completely heated and the convection streams within the sample stop, a special insert 4 is placed into the cuvette 2 so that the thrombogenic substance (coagulation activator) applied on the butt end of the insert 4 would touch the sample 3 and facilitate the initiation of the analyzed coagulation process. The following substances can be used to facilitate the initiation of the coagulation process: a protein, the so-called tissue factor (thromboplastin), immobilized by different means on the butt end surface of the insert 4 or directly on the inner surface of the cuvette 2 at a predefined place; as well as other organismic agents, such as preparations of cells and tissues. Other thrombogenic substances such as glass, kaolin, plastic, etc., can also be used as a coagulation activator.

Then, the temperature-controlled chamber 1 is closed using the pressurization means 6; excess pressure (not exceeding 0.2-0.5 atm as to the atmospheric one) is established and maintained throughout the temperature-controlled chamber through operation of the means of pressure adjustment 5. Excessive pressure is necessary to prevent formation of gas bubbles within the sample 3 and the thermal agent. This is necessary to prevent the said bubbles from distorting the results of registration of the optical parameters of the coagulation process (while illuminated, gas bubbles cause artifact spots of light). The means of pressure adjustment 5, in a particular case of manufacturing, can include an air pump, return valves, and a pressure sensor measuring pressure in chamber 1. The pressurization means 6 can be represented by a cover, cup, shutter, or any other common device. At that, the pressurization means 6 can be mechanical, locked by an operator, or electro-mechanical, operating according to the commands of a means of control.

The temperature-controlled chamber 1 is equipped with a transparent window 7 through which the cuvette with the test sample 3 is illuminated by means of illumination 8 and means of irradiation 12 with a different spectral range. The means of illumination 8 is intended to illuminate the sample in order to further register light scattering from the sample (e.g., the sample is illuminated within the red emission range). If necessary, several means of illumination (not shown on FIG. 1) can illuminate the cuvette 2 containing the sample 3 symmetrically from the sides. The means of irradiation 12 are intended to excite the fluorescence signal from a special fluorophore marker formed within the sample upon interaction of thrombin with the fluorogenic substrate previously added to the sample (e.g., the sample is illuminated within the wavelength range corresponding to the marker excitation range). LEDs (or groups of LEDs) as well as any other sources (or groups of sources) of irradiation of the required spectral range can be used as means of illumination and irradiation.

The process of coagulation is launched by contact of the coagulation activator applied on the end of insert 4 with the sample 3. The fibrin clot starts to grow from the end of the insert. Images of the process of fibrin clot formation are registered by the means of photo/video registration 9 (e.g., digital photo/video camera) using the lens 10 in the form of spatial distribution of the light scattering (photo) from the sample 3 illuminated by the means of illumination 8. The formed fibrin clot provides good light scattering while the plasma is virtually transparent to the light coming from the means of illumination 8. As a result, the fibrin clot on the image (photo) obtained by the means of registration of light scattering shall be brighter than the uncoagulated part of the sample (FIG. 2). During the test, the light trap 11 placed inside the temperature-controlled chamber 1 provides efficient absorption of light that comes from the means of illumination and reaches behind the cuvette 2 plane. This is achieved by the geometry and the surface parameters of the light trap providing repeated re-reflection of light by the trap walls and its gradual efficient absorption. The light trap can be designed in different ways, amongst others formed by specific geometry of the inner surfaces of the temperature-controlled chamber, in particular represented by a flattened cone. It can also be formed by conferring light absorbing features to the inner surfaces of the chamber, for example by darkening or making them somewhat rough. The geometry and optical features of the light trap 11 were figured out to provide repeated re-reflection and absorption of the background irradiation. Thus, only a minor part of the light that reaches behind the cuvette 2 plane during the sample illumination shall go back into the area of registration of the cuvette 2 and into the entrance aperture of the lens 10 upon reflection from the walls of the temperature-controlled chamber 1 and trap 11. This provides a better contrast range between the coagulated and uncoagulated parts of the sample. Through digital processing of the series of images (photos) of light scattering, the means 13 of processing of the test results calculates parameters of spatial dynamics of plasma coagulation (e.g., clot growth velocity, clot growth lag time, presence of spontaneous clots, etc.).

If before the beginning of the test, some fluorogenic substrate is added into the sample 3, to one of the proteolytic enzymes of the coagulation system, in particular, if the substrate is added to thrombin, this allows testing spatial kinetics of the given proteolytic enzyme, thrombin, within the process of plasma coagulation. When thrombin is formed in the sample, it starts cleaving the signal marker from the substrate. The marker can fluoresce while being radiated by light of a given wavelength (in particular, 370 nm). Spatial distribution of the thrombin concentration at different times can be obtained from the spatial distribution of the marker signal at different times using the reaction-diffusion equations.

To register spatial kinetics of the proteolytic enzyme during blood coagulation, the test sample 3 with added fluorogenic substrate is radiated at given times by means of irradiation 12 to excite fluorescence signal of the marker; images of spatial distribution of fluorescence of the marker in the sample (FIG. 2) are registered by the means of registration 9.

Figure 3:
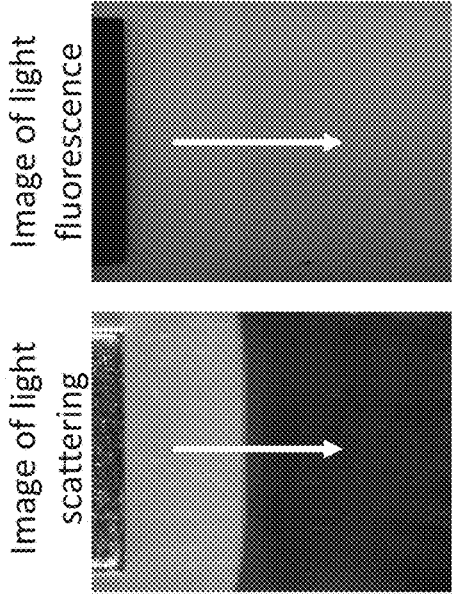
FIG. 3 provides an example of artifact distortion of the marker fluorescence signal at the fibrin clot border while using one means of irradiation irradiating the sample in direction perpendicular to the cuvette wall (left), as well as an example of elimination of the artifact distortion of the marker fluorescence signal at the fibrin clot border while using two means of irradiation (right)
Figure 3:
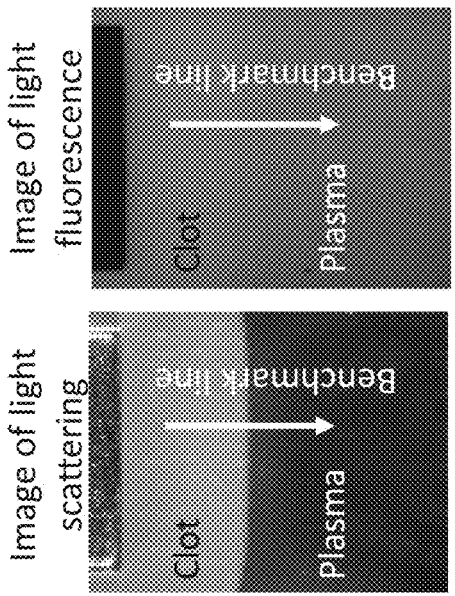
Figure 3:
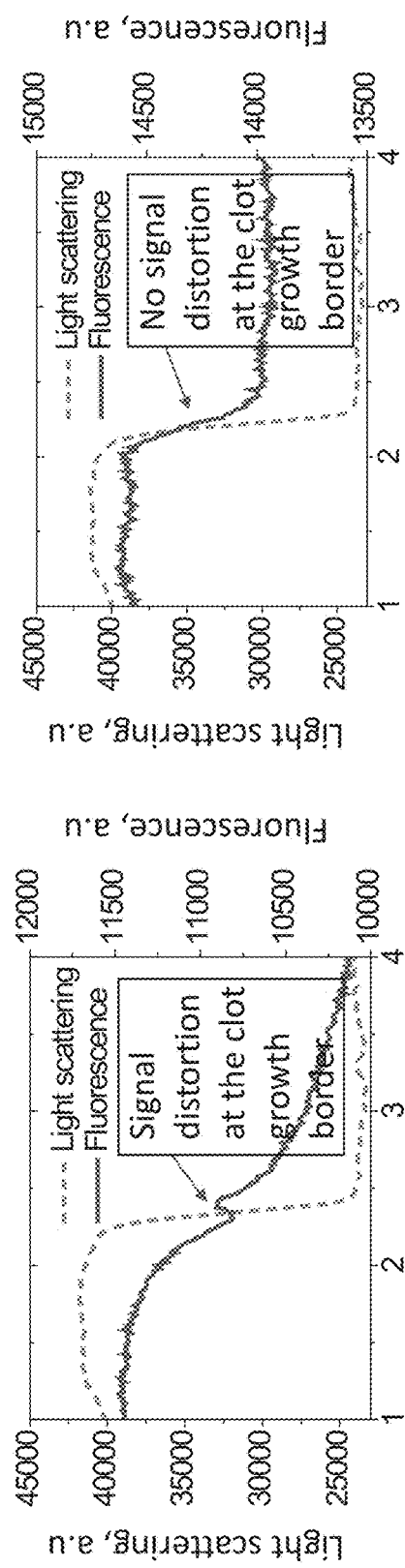

In order to obtain the claimed technical result, that is, in order to improve accuracy of determination of the spatial and temporal distribution of thrombin, the means of irradiation 12 are placed against the cuvette so as to eliminate the appearance of artifact distortions of the marker fluorescence signal at the border of fibrin clot growth (FIG. 3). One first means of irradiation 12 is radiating the cuvette 2 through the window 7 in the temperature-controlled chamber perpendicularly to the cuvette 2 wall: that is obtained by using a dichroic mirror 14 (a mirror used to illuminate the excitation, transparent so as to allow to study fluorescence); this location of the means 12 provides the most uniform irradiation of the cuvette. The second means of irradiation 12 is radiating the cuvette 2 through the window 7 at an angle from below, thus minimizing distortions of the marker fluorescence signal at the border of the fibrin clot growth. The irradiation from all the means of irradiation 12, each of which can be represented by several means of irradiation (not shown on FIG. 1) is undergoing spectral correction by filters 16 that provide isolation of the marker fluorescence signal spectrum from the spectrum of the means of illumination. Diffusors 17 are used to smooth the directional irradiation pattern of the means of irradiation 12. The light filter 15 is used to block the part of irradiation from the means of irradiation 12 reflected by the sample, cuvette, or chamber walls. The means of illumination 8 and/or the means of irradiation 12 are switched on only for a short time when the process of light scattering/fluorescence registration is on. This working pattern of the means of illumination/irradiation decreases the effect of photo discoloration of the substrate marker.

While irradiating the sample by the excitation irradiation, the fluorescent marker starts emitting light in a different wavelength range (fluorescence radiation). The marker fluorescence radiation is registered by the means of registration 9 (e.g., digital photo/video camera) using the lens 10 in the form of images of spatial distribution of the fluorescence signal (FIG. 2). Through digital processing of the series of fluorescence photos, the means 13 of processing of the test results calculates parameters of spatial kinetics of the proteolytic enzyme, in particular thrombin (e.g., thrombin distribution velocity, thrombin amplitude spike, quantity of thrombin formed, etc.).

Figure 4:
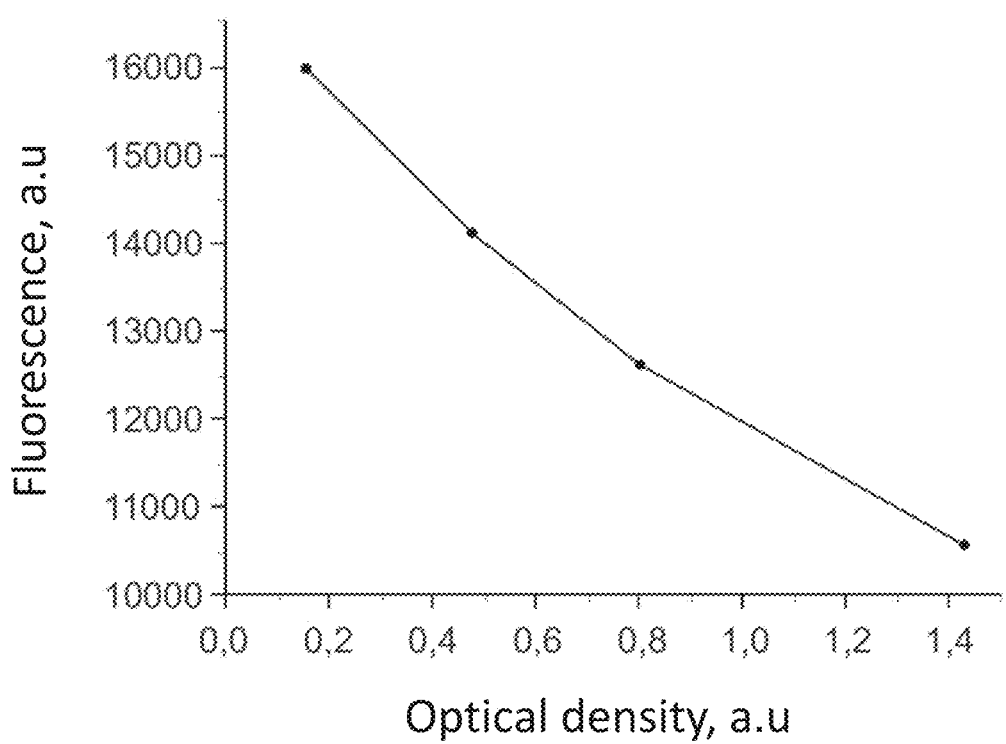
FIG. 4 shows the graph of dependency of the marker fluorescence signal intensity from the sample optical density.

The marker fluorescence signal depends not only on the proteolytic enzyme activity, but also on the optical parameters of the test sample 3. For normal samples (without evidence of hemolysis or chylous), the intensity of fluorescence of the specified marker concentration differs insignificantly, allowing the use of the same calibration for all normal samples (calibration is the dependence between the marker fluorescence intensity at any point of the sample and the concentration thereof once established for a specific device). However, the increased bilirubin or hemoglobin presence in the sample as well as the chylous parameters thereof modify the optical density of the sample, which at its turn influences the marker fluorescence signal. To use the same calibration for such samples, it has to be standardized in advance using the level of the sample optical density and the dependence of the marker fluorescence signal intensity on the sample optical density (FIG. 4). The level of optical density of the sample 3 is calculated based on the level of intensity of the excitation illumination signal from the means of irradiation 12 illuminating the cuvette perpendicularly and having passed through the sample. The signal intensity of the irradiation that has passed through is measured by an electronic photo detector 21. It is not recommended to place the electronic photo detector 21 inside the thermostat chamber 1 filled with the thermal agent while this will require measures for isolation of the electric part of the detector from the thermal agent (e.g., water) and those for waterproof output of the signal from the photo detector (cables) from the temperature-controlled chamber 1. Placing the photo detector 21 directly behind the cuvette 2 shall significantly distort the image of light scattering from the sample through formation of parasitic signals of light scattering and reflection from the photo detector 21. To avoid these issues, the photo detector 21 is placed outside the temperature-controlled chamber. At that, the excitation irradiation that has passed through the cuvette 2 is sent to the photo detector 21 by a mini mirror 19 through the transparent hermetically sealed window 20. The mirror 19 is structurally fixed in the cuvette retainer 18 and is located behind the cuvette 2 so that it distorts the light scattering and fluorescence signal of the sample only in a small part of the registration area that is not taken into account during further analysis. Thus, a part of excitation radiation that has passed through the sample 3 reaches the photo detector 21. The signal registered by the photo detector depends on the optical density of the sample and is used to standardize the calibration.

The registration of spatial dynamics of the coagulation process and of kinetics of the proteolytic enzyme formation is provided within the frame of the same analysis by the alternate use of the means of illumination 8 and irradiation 12.

Thus, the claimed device allows registration, at different times during the process of plasma sample coagulation, of the spatial distribution of light scattering from the sample and of fluorescence of the fluorophore marker formed through the action of thrombin, the proteolytic enzyme of the blood coagulation system. The parameters of the spatial dynamics of the fibrin clot growth and the spatial kinetics of the formation of thrombin are calculated via analysing of the obtained distributions. The resulting data provides important information about the status of the blood coagulation system of the sample.

The invention claimed is:

1. A device for monitoring spatial and temporal dynamics of thrombin that includes: a temperature-controlled sealed chamber with a transparent window and a light trap, said temperature-controlled sealed chamber being filled with a fluid medium and designed to be capable of accommodating a cuvette containing a test sample of blood plasma, and a coagulation activating insert placed into the cuvette, the coagulation activating insert contains a butt end, wherein a substance applied to the butt end initiates a coagulation process, at least one means of illumination of the sample designed to be capable of exciting a light scattering signal from the sample, at least one first means of irradiation and at least one second means of irradiation, a means of optical photo/video registration of light scattering/irradiation from the sample, and a means for adjustment of pressure in the temperature-controlled sealed chamber designed to be capable of maintaining the pressure inside the temperature-controlled sealed chamber exceeding atmospheric pressure, wherein the at least one first means of irradiation is designed to be capable of exciting a fluorescence signal of a special marker that forms in the sample during cleavage of a fluorogenic substrate previously added to the sample by one of proteolytic enzymes of the coagulation system and the at least one second means of irradiation of the sample is designed to be capable of exciting the fluorescence signal of the said marker, where the at least one first means of irradiation provides irradiation of the sample through the transparent window in a direction perpendicular to a cuvette plane, and the at least one second means of irradiation provides irradiation of the sample through the transparent window at an angle to the cuvette plane from below the cuvette, wherein the butt end of the coagulation activating insert and a growing fibrin clot are irradiated, and wherein the at least one first means of irradiation and the at least one second means of irradiation have the same spectral range of irradiation that differs from the spectral range of the at least one means of illumination, and wherein the first and the second means of irradiation are switched on at the same time.

2. The device according to claim 1, wherein the device further comprises a means of analysis of optical density in the sample.

3. The device according to claim 1, wherein the means for adjustment of pressure is designed to maintain excess pressure within the temperature-controlled sealed chamber, wherein the excess pressure is 0.2-0.5 atm higher than the atmospheric pressure.

4. The device according to claim 1, wherein the device further comprises optical elements that direct, focus, and provide spectral correction of illumination/irradiation.

5. The device according to claim 1, wherein the device further comprises a means of control programmed to synchronize operation of the at least one means of illumination, the at least one first means of irradiation and the at least one second means of irradiation, the means of optical photo/video registration and the means for adjustment of pressure.

6. The device according to claim 2, wherein the means of analysis of the sample optical density is designed to perform the analysis at fluorescence marker excitation wavelength.

7. The device according to claim 1, wherein the at least one means of illumination is a source capable of illuminating the sample within the red emission range.

* * * * *